US007583782B2

(12) United States Patent
Yamazaki

(10) Patent No.: US 7,583,782 B2
(45) Date of Patent: Sep. 1, 2009

(54) X-RAY CT APPARATUS AND AN IMAGE CONTROLLING METHOD THEREOF

(75) Inventor: Masahiko Yamazaki, Tochigi-ken (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 11/617,236

(22) Filed: Dec. 28, 2006

(65) Prior Publication Data

US 2007/0147576 A1    Jun. 28, 2007

(30) Foreign Application Priority Data

Dec. 28, 2005    (JP)    ............... 2005-379929

(51) Int. Cl.
*A61B 6/00*    (2006.01)

(52) U.S. Cl. .......................... 378/4; 378/147

(58) Field of Classification Search ............ 378/4, 378/147, 901
See application file for complete search history.

(56) References Cited

U.S. PATENT DOCUMENTS

| 4,442,489 | A | * | 4/1984 | Wagner | 378/19 |
|---|---|---|---|---|---|
| 6,023,494 | A | * | 2/2000 | Senzig et al. | 378/4 |
| 6,246,742 | B1 | * | 6/2001 | Besson et al. | 378/8 |
| 6,275,562 | B1 | * | 8/2001 | He et al. | 378/19 |
| 6,385,278 | B1 | * | 5/2002 | Hsieh | 378/8 |
| 6,445,761 | B1 | * | 9/2002 | Miyazaki et al. | 378/8 |
| 6,700,948 | B2 | | 3/2004 | Hoffman | |
| 6,834,097 | B2 | * | 12/2004 | Yamazaki | 378/19 |
| 2003/0076920 | A1 | * | 4/2003 | Shinno et al. | 378/4 |
| 2004/0202283 | A1 | * | 10/2004 | Okumura et al. | 378/145 |
| 2007/0019779 | A1 | * | 1/2007 | Nishide et al. | 378/4 |

* cited by examiner

*Primary Examiner*—Edward J Glick
*Assistant Examiner*—Alexander H Taningco
(74) *Attorney, Agent, or Firm*—Oblon, Spivak, McClelland, Maier & Neustadt, P.C.

(57) ABSTRACT

An X-ray CT apparatus and image controlling method thereof that achieves a higher time resolution tomography image on a region of interest (ROI) of an object while reducing a total amount of X-ray irradiation exposure. The X-ray CT apparatus includes an X-ray source for irradiating X-rays over an object, a multi-slice detector provided facing to the X-ray source for acquiring wide range projection data by a first helical scan, a wide range projection data memory unit for storing the wide range projection data, and a narrow range projection data memory unit for storing the narrow range projection data of a designated region of interest (ROI) only. A controlling method for the X-ray CT apparatus acquires narrow range projection data by a second scan on the ROI along a slice direction and generates compounded projection data based on the narrow range projection data and the wide range projection data. The method generates images based on the compounded projection data.

11 Claims, 5 Drawing Sheets

SLICE DIRECTION

X-RAY CT APPARATUS AND AN IMAGE CONTROLLING METHOD THEREOF

CROSS-REFERENCE TO RELATED APPLICATIONS

This application claims priority from, and the benefit of, Japanese Patent Application No. 2005-379929, filed on Dec. 28, 2005, the contents of which are expressly incorporated herein by reference in their entirety.

BACKGROUND OF THE INVENTION

1. Field of the Invention

The present invention relates to an X-ray computer tomography (CT) apparatus and an image controlling method thereof, and more particularly, to an X-ray CT imaging apparatus and an image controlling method thereof that can obtain a tomography image of higher time resolution for a selected area of region of interest (ROI) than peripheral areas of the ROI by using a two-dimensional multi-slice detector to reduce X-ray exposure amount of an object.

2. Background of the Invention

In an X-ray CT imaging apparatus having a multi-slice detector, an X-ray source irradiates a fan-shaped X-ray beam over an object and X-ray amounts penetrated through an object are detected by each of elements of the detector provided at an opposite position of the X-ray source. The detected projection data is reconstructed to display tomography images. A two dimensional multi-slice detector including a plurality of channels along a traversing direction (x-axis) of the object has a z-axis corresponding to an image slice (row) direction so as to form an arc shaped configuration in a direction traversing the z-axis. An X-ray source and a multi-slice detector are provided in a gantry so as to be located at opposite positions with respect to each other, and are rotated around an object placed at a center position of the gantry. By rotating an X-ray source and a multi-slice detector around an object in different angles, a series of views are obtained. This operation is referred to as a "scan".

A helical scan rotates an X-ray source and a multi-slice detector around an object with shifting the gantry along a z-axis of the apparatus so as to obtain projection data through the multi-slice detector to reconstruct a tomography of an object.

Once a total tomography image of diagnosis portion of an object is acquired by using an X-ray CT imaging apparatus including a two dimensional multi-slice detector, an operator or a doctor decides a particular diagnosis portion in the total tomography image (hereinafter referred to as a "region of interest (ROI)"). For example, a cardiac portion is selected as an ROI. It is a technology to successively perform a plurality of scans in order to obtain dynamic images of a cardiac as an ROI or to obtain a three dimensional (3D) image data by collecting a plurality of projection data of the same phases through a cardiac synchronized reconstruction process.

However, in the background technology, while it is required to obtain projection data of a narrow range covering an ROI only in a total tomography image of an object, it has been necessary to perform a plurality of scans to obtain wide range projection data of a whole diagnosis portion including an ROI to obtain higher time resolution images. Consequently, the background technology has serious problems and defects of needing an increase of exposure amount to an object to obtain higher time resolution images of a cardiac dynamic image.

SUMMARY OF THE INVENTION

The present invention is capable of solving the above-mentioned problems and defects of the background X-ray CT imaging apparatus. The present invention provides an X-ray apparatus and an image controlling method thereof that can obtain projection data of a higher time resolution as to a relatively small area of a region of interest (ROI) in an object while reducing exposure amount of radiation to the object. Thus, the X-ray CT imaging apparatus and an image controlling method can reconstruct dynamic images of the ROI with restricting an exposure amount of X-ray radiation to an object.

According to one embodiment of the present invention, an X-ray CT apparatus comprises: an collimator driving unit configured to control irradiated X-rays; a multi-slice detector provided at a position facing to the X-ray source to detect the irradiated X-rays through an object; a wide range projection data control unit configured to acquire wide range projection data by irradiating X-rays from the X-ray source onto a wide range that is controlled by the reduction area driving unit so as to cover peripheral channel portions of the multi-slice detector; a wide range projection data memory unit configured to store the acquired wide range projection data; a narrow range projection data control unit configured to acquire narrow range projection data by irradiating X-rays from the X-ray source onto a narrow range that is controlled by the collimator driving unit so as to cover central channel portions of the multi-slice detector after the acquisition of the wide range projection data; and a reconstruction unit configured to generate compounded projection data based on the wide range projection data and the narrow range projection data, and to perform a reconstruction process based on the compounded projection data According to another embodiment of the present invention, a an X-ray source configured to irradiate X-rays on an object; a multi-slice detector provided facing to the X-ray source so as to acquire wide range projection data of the X-rays through an object at a first range along an image slice direction; a wide range projection data acquiring memory unit configured to store the wide range projection data by the multi-slice detector; a narrow range projection data memory unit configured to store narrow range projection data that is acquired through the multi-slice detector by irradiating the X-rays from the X-ray source on a narrow range portion including a designated a region of interest (ROI); and a composition unit configured to generate projection data based on the wide range projection data supplied from the wide range projection data memory unit and the narrow range projection data supplied from the narrow range projection data memory unit.

According to another embodiment of the present invention, an X-ray CT apparatus comprises: an object X-ray source configured to irradiate X-rays; an image storing unit configured to store volume data of X-ray CT images; a projection data generating unit configured to generate wide range projection data from the volume data; a control unit configured to acquire narrow range projection data by irradiating X-rays from the X-ray source onto a region of interest (ROI); and a reconstruction unit configured to perform a compounding process based on the wide range projection data generated by the projection data generating unit and the narrow range projection data, and to perform reconstruction processes based on the projection data obtained by the compounding.

According to another embodiment of the present invention, a controlling method controls an X-ray CT apparatus including an X-ray source for irradiating X-rays onto an object, a multi-slice detector for detecting the X-rays penetrated through the object, and a reconstruction unit for reconstructing images based on the projection data collected through the multi-slice detector. The image controlling method comprises: executing a helical scan over a whole diagnosis portion of an object; collecting wide range projection data of the helical scan through the multi-slice detector; displaying wide range tomography images by performing reconstruction processes based on the wide range projection data; designating a region of interest (ROI) in the displayed wide range tomography image; acquiring narrow range projection data by executing a volume scan on the designated ROI; generating wide range projection data from the reconstructed image data; compounding the generated wide range projection data with the narrow range projection data; and displaying images by performing a reconstruction process of the compounded data.

According to another embodiment of the present invention, a controlling method controls an X-ray CT apparatus including an X-ray source for irradiating X-rays onto an object, a multi-slice detector for detecting the X-rays penetrated through the object, and a reconstruction unit for reconstructing images based on projection data through the multi-slice detector. The controlling method comprises: collecting wide range projection data through a helical scan by irradiating the X-rays along a wide channel direction; collecting narrow range projection data through a volume scan by irradiating the X-rays on a region of interest (ROI) with a narrow width along the channel direction and with a wider width than the narrow width along an image slice direction; converting projection data from the wide range projection data so that the converted projection data passes the same X-ray path of an X-ray path of the narrow range projection data; compounding the converted wide range projection data with the narrow range projection data; and performing a reconstruction process based on the compounded projection data.

BRIEF DESCRIPTION OF THE DRAWINGS

The accompanying drawings, which are incorporated in and constitute part of this specification, illustrate various embodiments and/or features of the present invention, and together with the description, serve to explain the present invention. Where possible, the same reference numbers will be used throughout the drawings to describe the same or like parts. In the drawings.

DESCRIPTION OF THE PREFERRED EMBODIMENTS

With reference to the following FIGS. 1-5, embodiments consistent with the present invention will be explained. As an exemplary embodiment of an X-ray CT apparatus consistent with the present invention, a two dimensional multi-slice X-ray CT apparatus is explained.

Figure 1:
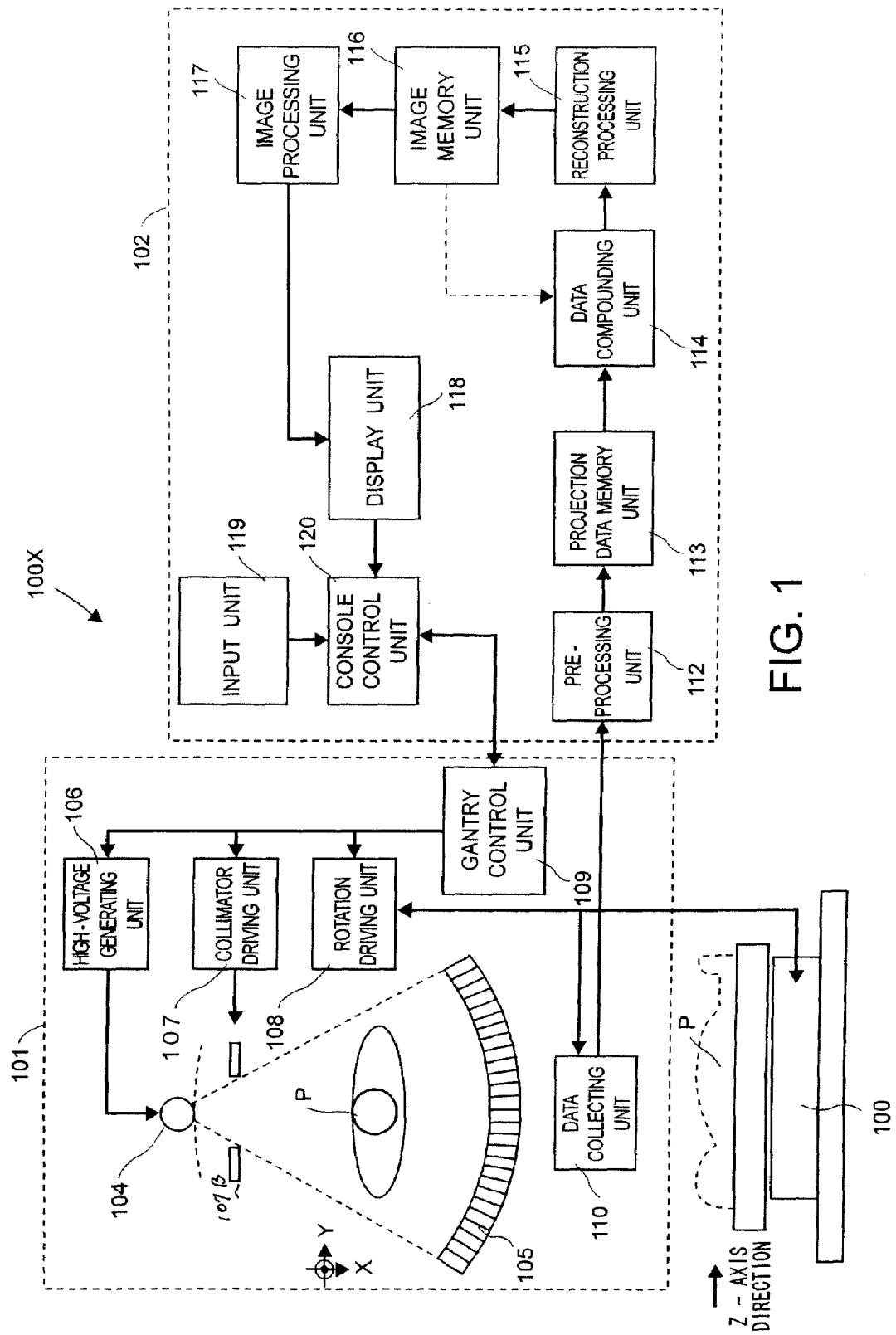
FIG. 1 is a block diagram illustrating a construction of an X-ray CT apparatus consistent with one embodiment of the present invention.

FIG. 1 shows a block diagram of the construction of the multi-slice X-ray CT apparatus 100X. X-ray CT apparatus 100X includes a bed apparatus 100 having a top plate for supporting an object P, a gantry unit 101 configured to collect X-ray projection data by operating together with movements of the top plate, and a data processing and displaying unit 102. At the gantry unit 101, X-ray source 104 irradiates X-rays upon an object P. The penetrated X-rays through the object P are collected through the detector 105 as projection data. The collected projection data is supplied to the data processing and displaying unit 102. In the data processing and displaying unit 102, a data processing operation is performed based on the projection data so as to display CT images of desired portions of the object P on a display apparatus 118 in the data processing and displaying unit 102.

In the gantry unit 101 of the X-ray CT apparatus 100X, an X-ray source 104 for irradiating X-rays and a two dimensional multi-slice detector 105 positioned facing to the X-ray source 104 to detect X-rays penetrated through an the object P are provided in the gantry unit 101. The two dimensional multi-slice detector 10 is constructed by, for example, a plurality of channels arranging a plurality of X-ray detector elements into a wide angle of fan beams from the X-ray source 104 and also arranging a plurality of X-ray detector elements along an image slice direction, i.e., row direction of a channel. The gantry unit 101 further includes a high-voltage generating unit 106 for supplying a high voltage to the X-ray source 104, a collimator driving unit 107 for adjusting or controlling an X-ray irradiation area onto the object P from X-ray source 104, a rotation driving unit 108 for rotating a pair of the X-ray source 104 and the multi-slice detector 105 in the gantry, a gantry control unit 109 for controlling driving of the bed apparatus 100 and the gantry unit 101 supporting the object P, and a bed and a data collection unit 110 for collecting X-ray projection data detected through the multi-slice detector 105. The collimator driving unit 107 drives a collimator unit 107B for adjusting an X-ray irradiation area. The collimator unit 107B includes a pair of collimator blades provided along a channel direction and a pair of collimator blades provided along a slice direction.

The data processing and displaying unit 102 in the X-ray CT apparatus 100X includes a pre-processing unit 112 for executing pre-processing of X-ray projection data supplied from the data collection unit 110 in the gantry unit 101, a projection data memory unit 113 for storing the pre-processed X-ray projection data, a data composition unit 114 for compounding projection data from the projection data memory unit 113, as explained later, a reconstruction process unit 115 for reconstructing data based on the compounded projection data from the data compounding unit 114, an image memory unit 116 for storing reconstructed volume data in the reconstruction process unit 115, an image processing unit 117 for processing image display operations based on volume data stored in the image memory unit 116, a display unit 118 for displaying tomography data processed in the image processing unit 117, an input operation unit 119 for designating a region of interest (ROI) in a tomography displayed on the display unit 118 and a console control unit 120 for controlling input operation performed by an operator through the input operation unit 119 and various display controls on the data processing and displaying unit (console) 102.

Figure 2:
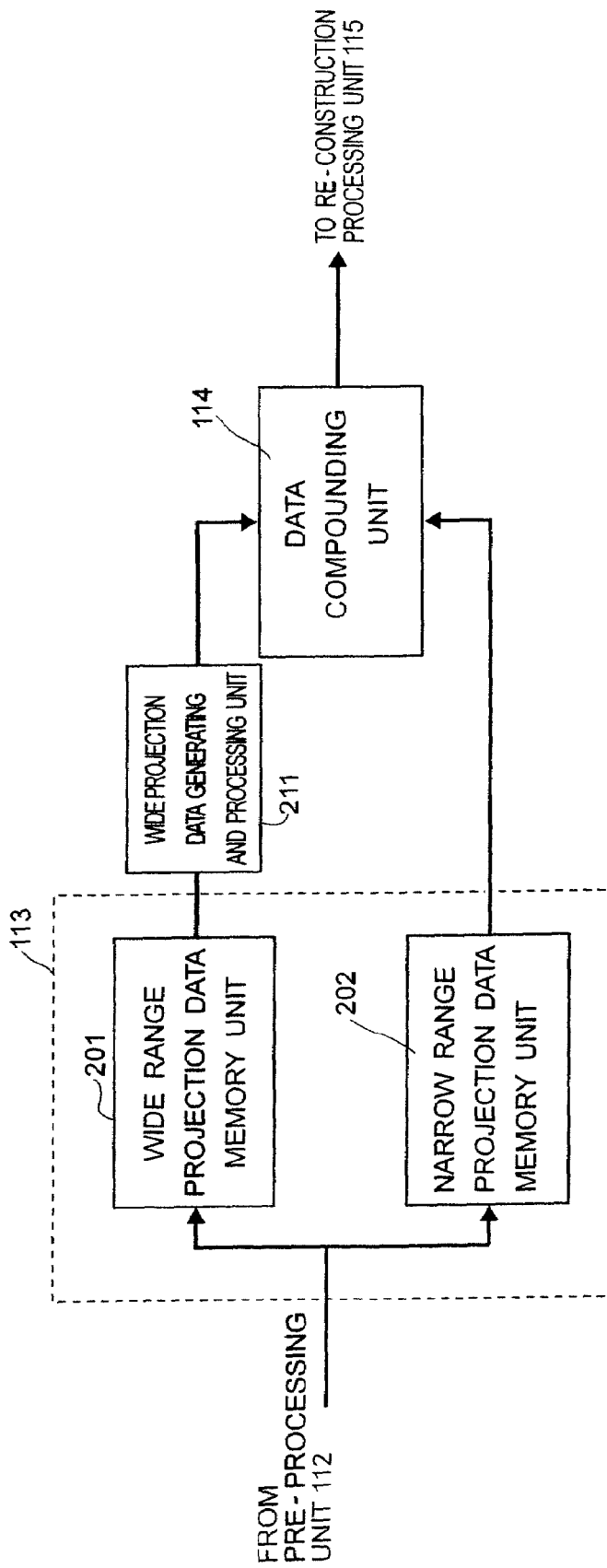
FIG. 2 illustrates a construction of the projection data memory unit in the X-ray CT apparatus shown in FIG. 1.

FIG. 2 explains a construction and operations of the projection data memory unit 113 and the data compounding unit 114 shown in FIG. 1. As shown in FIG. 2, the projection data memory unit 113 in the data processing and displaying unit 102 of X-ray apparatus 100X consistent with the present invention includes a wide range projection data memory unit 201 and a narrow range projection data memory unit 202. A wide projection data processing/generating unit 211 is provided between the wide range projection data memory unit 210 and the data compounding unit 114.

Firstly, a first X-ray scan is executed to acquire and store wide range projection data by using a wide width of the multi-channel detector along a channel direction for covering a whole diagnosis area of the object P. Wide range projection data output from the wide range projection data memory unit 201 is supplied to a reconstruction process unit (not shown) provided in the wide projection data memory unit 201 or directly supplied to the reconstruction processing unit 115 to reconstruct and display on the display unit 118 as a wide range tomography. With viewing the wide range tomography, an operator or a doctor designates a region of interest (ROI), for instance a cardiac portion, in the wide range tomography through the input unit 119.

Next, a second X-ray scan is executed with a fan beam of narrow range channel width for covering the designated ROI only by driving the collimator (reduction area) driving unit in the gantry unit 101. To acquire and store narrow range projection data, the second scan is executed so as to always locate the designated ROI at a center of a scanning width. The wide range projection data output from the wide range projection data memory unit 201 is supplied to a reconstruction processing unit (not shown) provided in the wide range projection data memory unit 201 or is directly supplied the reconstruction processing unit 115 and is converted to an image.

After converting images, the projection data processing/generating unit 211 converts the image to projection data. To compound with the narrow range projection data outputted from the narrow range projection data memory 202, at a data composition unit 114, the wide range projection data and the narrow range projection data are compounded such that each X-ray path for the wide range projection data passes the same X-ray path for the narrow range projection data. The compounded data is supplied to the reconstruction processing unit 115. It is noted that the wide range projection data and the narrow range projection data have different X-ray paths due to a difference of the respective cone angle of X-rays or a difference of the respective focusing position. Accordingly, to collect these differences of X-ray paths, in the X-ray CT apparatus consistent with the present invention, hypothetical projection data for covering the peripheral portions of the narrow range projection data can be generated by performing a projection process once after reconstructing the wide range projection data to images.

Figure 3:
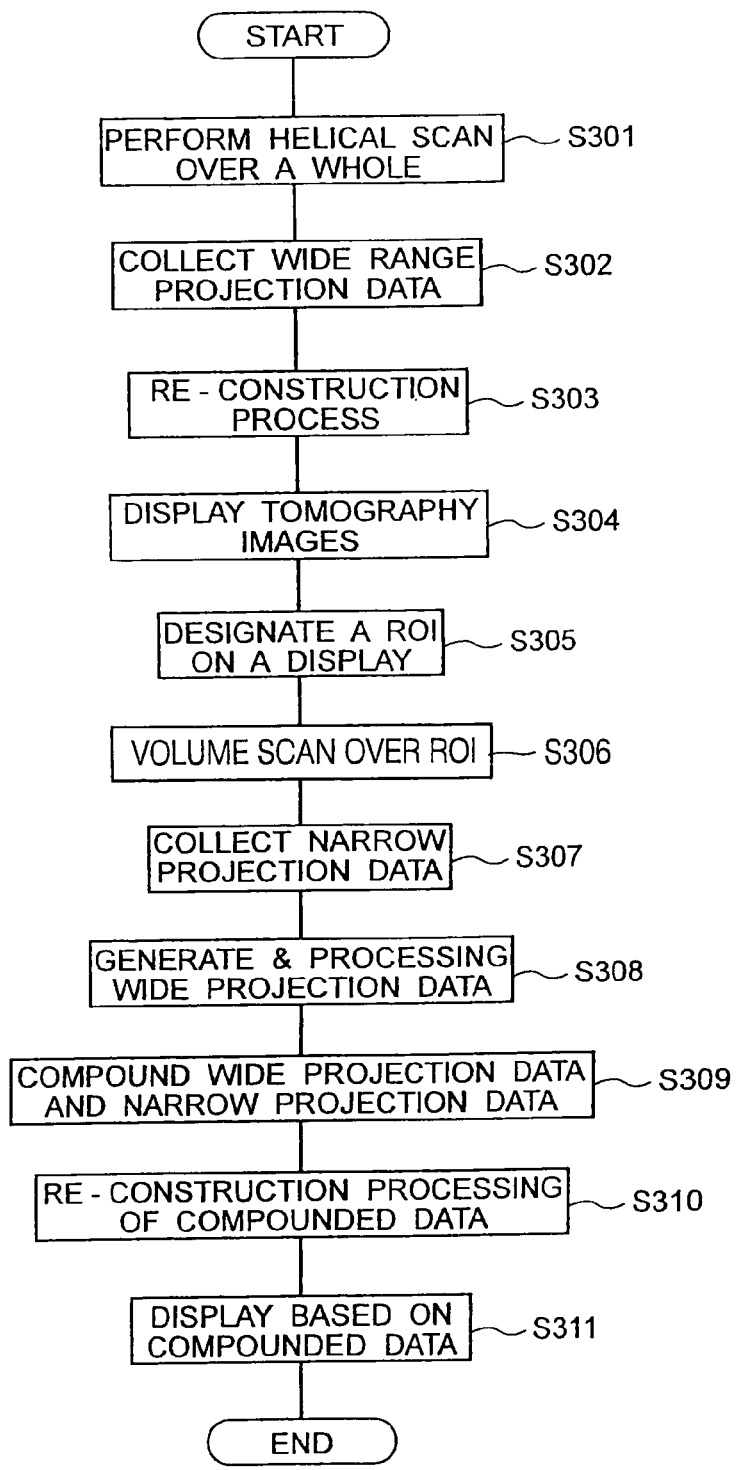
FIG. 3 is a flowchart for explaining one embodiment of an X-ray CT image processing method consistent with one embodiment of the present invention.

FIG. 3 is a flowchart for explaining an embodiment of an image processing method for the multi-slice X-ray CT apparatus consistent with the present invention. The object P laying on the top plate top plate of the bed 100 is moved in a body axis (z-axis shown in FIG. 1) direction into the center portion in the gantry unit 101 so as to placed at a predetermined position in the gantry unit 101. Firstly, X-ray source 104 irradiates X-ray beams over the object P with a wide range of channel width so as to cover the whole imaging area. By the wide range irradiation of X-ray beams, a helical scan is performed with moving the object P along a z-axis. Thus, the multi-slice detector 105 obtains wide range projection data (step S301).

The wide range projection data acquired through the helical scan is collected by the data collection unit 110 in the gantry unit 101 (step S302). The collected wide range projection data undergoes a pre-processing operation at a pre-processing unit 112 in the data processing and displaying unit 102 and is stored in a wide range projection data memory unit 201 of the projection data memory unit 113. The stored wide range projection data is supplied to the reconstruction processing unit 115 through the data compounding unit 114 to perform a reconstruction process (step S303). The reconstructed wide range projection data is once stored as volume data in the image memory unit 116. The reconstructed wide range projection data undergoes an imaging process in the image processing unit 117 and is then displayed as a tomography image on the display unit 118 (step S304).

Figure 4B:
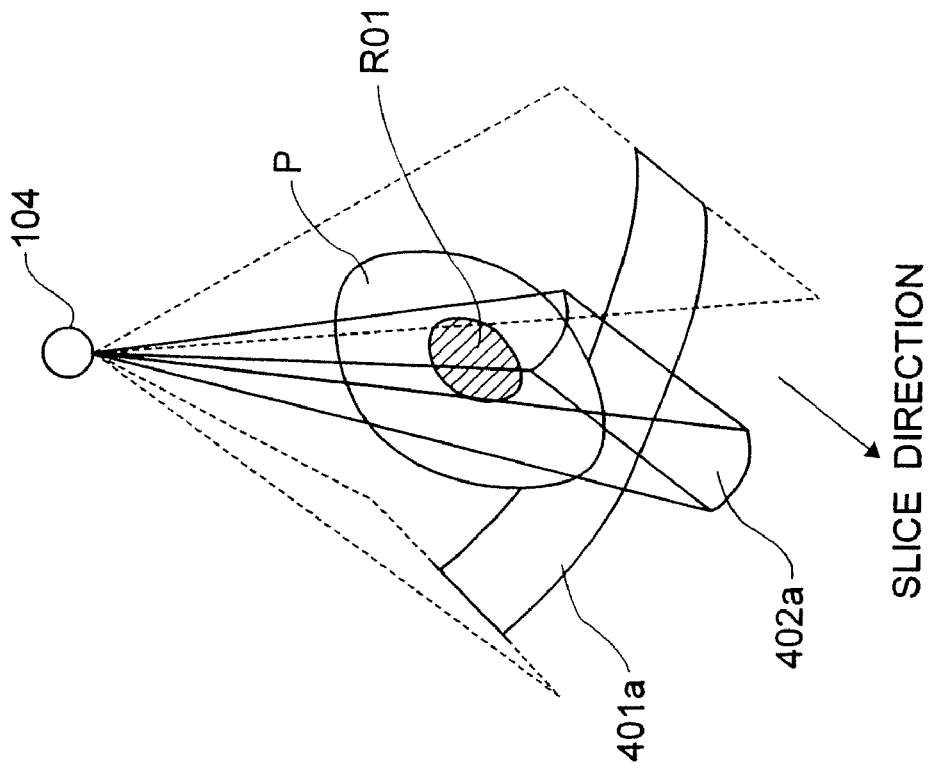
FIG. 4B illustrates a perspective view of X-ray fan beams and the arc-shaped multi-channel detector for explaining acquisition of narrow range projection data of a region of interest (ROI) with a higher time resolution at central channel portions of the multi-channel detector and for explaining acquisition of acquisition of range projection data of other areas excepting the ROI at peripheral portions of the detector so as to reduce an exposure amount.
Figure 4A:
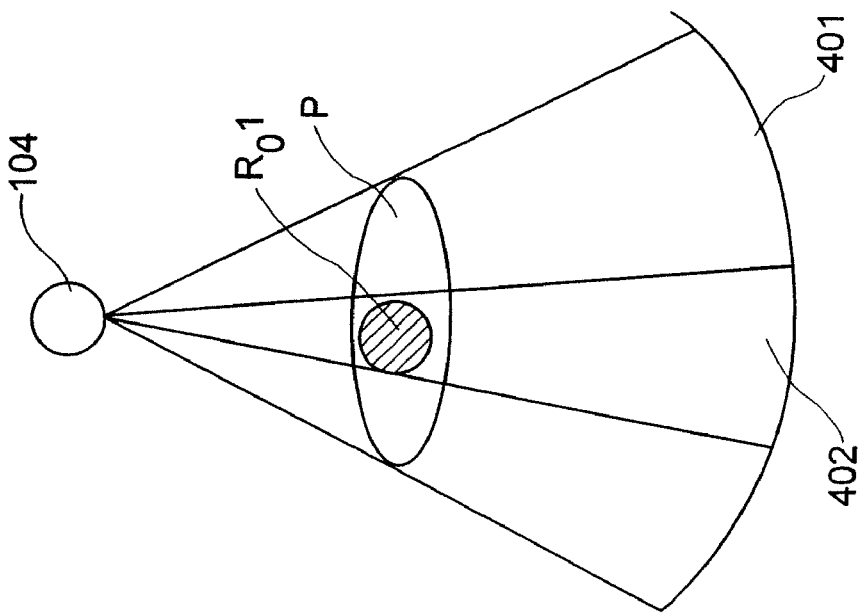
FIG. 4A illustrates a cross-section view of wide X-ray fan beams and an arc-shaped multi-channel detector for acquiring wide range projection data.

FIG. 4A is a cross-sectional view along a scanning direction, i.e., a detector channel direction, of irradiation of X-ray beams. FIG. 4B is a perspective view of irradiation of FIG. 4A along an image slice direction, i.e., a detector row direction. The wide range projection data of a wide area 401 is acquired, as shown in FIG. 4A, through the wide area 401 of the multi-slice detector 105 that covers all the channels of the detector along a channel direction, and also acquired, as shown in FIG. 4B, through relatively short row detector elements along an image slice direction, for instance 60 rows. On the other hand, the narrow range projection data of the narrow area 402 is acquired, as shown in FIG. 4A, through a narrow width of channels of the multi-slice detector 105 with covering an ROI always at channel center portions along a detector channel direction, and also acquired through a longer detector elements than the wide range detector elements for the wide area 401 so as to cover the ROI in an image slice direction by a plurality of rows, for instance, 200 rows.

Returning to FIG. 3, firstly, a first helical scan for a wide area 401 is performed so as to cover, for instance, a whole breast portion of the object P including an ROI, for instance, such as a heart. Thus, wide range projection data of the wide area 401 is acquired through the multi-channel detector 105 of a wide width along a channel direction and of a short width along a slice direction. The wide range projection data is displayed on a display after performing a reconstruction process. With viewing the displayed tomography image based on the wide range projection data, an operator or a doctor designates a region of interest (ROI), for instance a cardiac portion, that is required to be much more precisely examined by a dynamic image or a static image through an input apparatus, such as a mouse or a keyboard (step S305).

Once the ROI is designated in the tomography image based on the wide range projection data, the collimator driving unit drives the collimator unit 107B so as to cover the ROI portion only. Then, a second scan is performed by controlling X-ray beam irradiation onto the narrow range area 402 only. Thus, the second scan is, as shown in FIG. 4B, performed as a volume scan through the narrow area 402a of the multi-slice detector 105 that includes a shorter channel width along a channel direction and a longer width than the wide area 401a along a slice direction (step S306). The volume data is acquired by scanning the narrow area 402 without moving an object along a body axis (z-axis).

As mentioned above, the first scan for acquiring wide range projection data of the wide area 401 uses a multi-slice detector having a relatively narrow width along a slice direction, for instance of a plurality of detector elements of 60 rows. On the other hand, the second scan for acquiring narrow range projection data of the narrow area 402 for covering the ROI uses a multi-slice detector having a relatively longer width than the detector for the wide area 401 along a slice direction, for instance of a plurality of detector elements of 200 rows. Consequently, it becomes possible to acquire narrow projection data of a higher time resolution for the ROI by performing the second volume scan on the ROI.

Returning to the flowchart in FIG. 3, as explained above, the collimator (reduction area) driving unit 107 drives the collimator unit 107B to reduce an irradiation width of X-ray beams from the X-ray source 104 so as to place the ROI in the center portion of the irradiation to detect narrow projection data for the narrow area 402 through the second volume scan (step S306). The acquired narrow range projection data through the volume scan is collected in the data collection unit 110 (step S307). The narrow range projection data is processed in the pre-processing unit 112 and stored in the narrow range projection data memory unit 202 of the projection data memory unit 113. On the other hand, the wide range projection data acquired by the first helical scan and stored in the wide range projection data memory unit 201 is reconstructed into images at the reconstruction process of the step S303. After reconstructing into images, the wide range projection data is again converted from the image in the wide range projection data generating/processing unit 211 to be supplied to the data compounding unit 114. In this conversion, projection data passes on the same X-ray paths to X-ray paths around edge portions of the narrow range projection data from the reconstructed image based on the wide range projection data (step S308). The data compounding unit 114 compounds the re-generated wide range projection data with the narrow range projection data stored in the narrow range projection data memory unit 202 (step S309). Thus, the narrow range projection data for the ROI with a higher time resolution is compounded with the wide range projection data. The composition is performed by using the wide range projection data converted at the step S308 and the narrow range projection data.

The compounded projection data is processed in the reconstruction processing unit 115 (step S310). In the reconstruction process, the ROI portion is performed based on the narrow range projection data that is acquired by the second scan, and other area portions excepting the ROI are obtained by a calculation of the wide range projection data stored in the wide range projection data memory unit 201.

The reconstructed compounded data in the reconstruction processing unit 115 is stored in the image memory unit 116 and is also supplied to the image processing unit 117 to display the compounded images on a screen of the display unit 118 through an appropriate process for an image display (step S311). Consequently, it becomes possible to display the ROI only with a higher time resolution than the peripheral portions in the whole display of the wide range image.

According to the embodiment consistent with the present invention, the narrow range portion only for covering the ROI is twice irradiated by X-ray beams by long rows of a channel along a slice direction. However, the other wide area excepting the ROI portion is irradiated only once by X-ray beams by short rows of a channel along a slice direction. Consequently, the total amount of X-rays exposure can be reduced while enhancing a time resolution for the ROI.

In the above-mentioned embodiment, the wide range projection data and the narrow range projection data are compounded in the data compounding unit 114. After the compounding, the compounded data is processed in the reconstruction processing unit 115 and supplied to the image memory unit 116. As another embodiment, as explained later with respect to FIG. 5, it is also possible to use the volume data that has already been acquired by the first helical scan and stored in the image memory unit 116 as the wide range projection data to compound with the narrow range projection data. Thus, the wide range projection data is re-generated by performing generating/processing operations for the projection data. Thus, it is possible to compound the re-generated wide range projection data and the narrow range projection data to use in the reconstruction process.

As the multi-slice detector for using the X-ray apparatus consistent with the present invention, as shown in FIG. 4B, it is possible to use a cross-configured multi-slice detector that has a short width along a slice direction and a wide width along a channel direction and that further has a cross configuration of a wide width along the slice direction and a short width along the channel direction. In this case, it is also possible to compound the narrow range projection data with the wide range projection data detected by the wide width of the detector or the volume data based on the wide range projection data to perform a reconstruction process.

Figure 5:
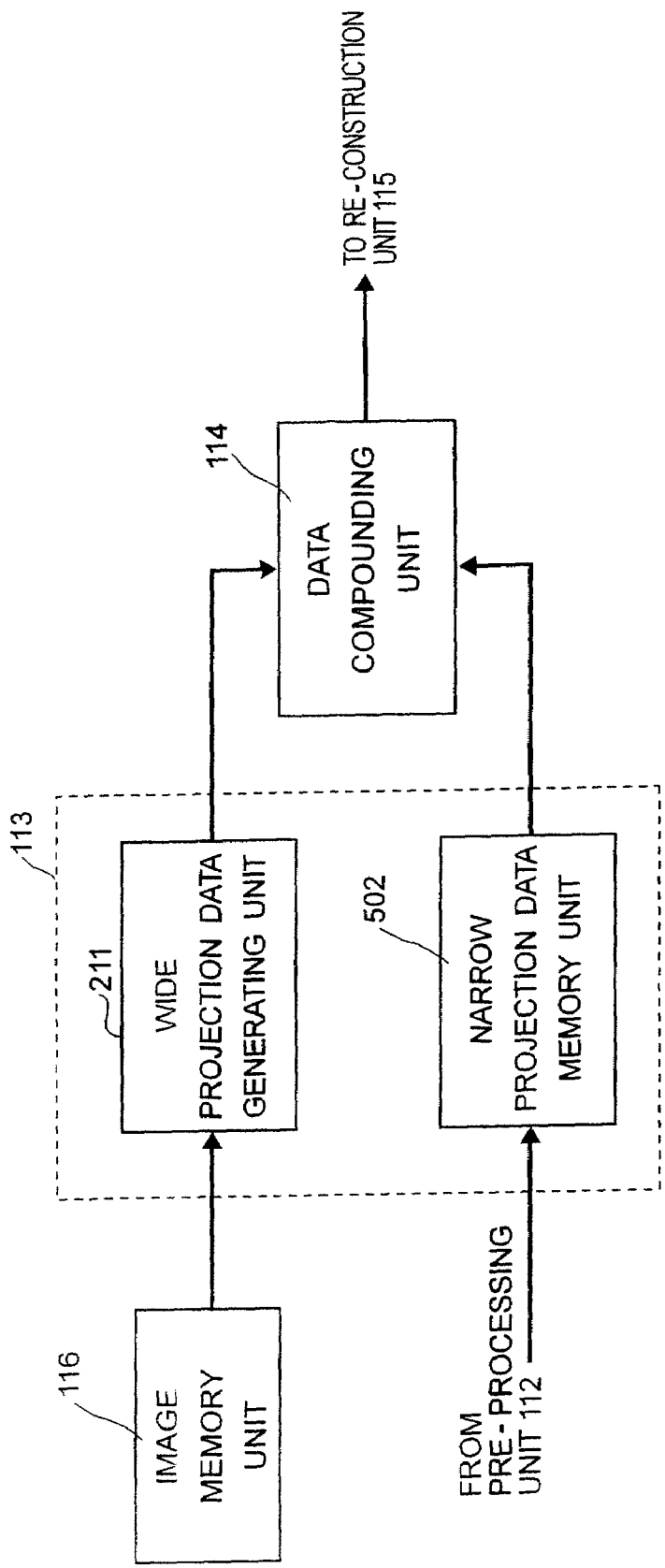
FIG. 5 is a block diagram illustrating another embodiment of a construction of an X-ray CT apparatus consistent with the present invention.

FIG. 5 is a block diagram for illustrating another embodiment of the data compounding in the multi-slice X-ray CT apparatus consistent with the present invention. As mentioned above, in this embodiment, the wide range projection data acquired by the first helical scan is stored as volume data in the image memory unit 116 after performing a reconstruction process. The stored data is re-generated as the wide range projection data in a wide range projection data generation unit 211 provided in the projection data memory 113. While, in this embodiment, the image data stored in the image memory unit 116 is generated at a present inspection, of course it is possible to generate the data acquired at a past inspection.

On the other hand, the narrow range projection data for the ROI is stored in the narrow range projection data memory unit 502 similar to the above-explained embodiment. The narrow range projection data and the projection data generated in the wide range projection data generation unit 211 are compounded in the data compounding unit 114. The compounded projection data is reconstructed in the reconstruction processing unit 115. Thus, it is possible to compound the narrow range projection data of the ROI with the wide range projection data that has already used for a reconstruction process without repeating the first helical scan.

In the above-explained embodiments, a cross-configured multi-slice detector is used. Of course, it is possible to use any type of multi-slice detector for detecting X-ray beams in the X-ray apparatus consistent with the present invention. For instance, as shown in FIG. 4B, by dotted lines, it is possible to use a wide range detector that has the same wide width of rows along an image slice direction as the wide width of rows for the narrow range detector.

Further, in the above-explained embodiments, the peripheral data for the narrow projection data is presumed by performing a projection process after once reconstructing into images. Of course, it is possible to presume the projection data at peripheries of the narrow projection data from the collected wide projection data without performing a reconstruction process. For instance, it is possible to convert fan beam-shaped wide and narrow range projection data into projection data of parallel beams and to presume the projection data for the peripheral portions of the narrow range projection data of parallel beams from the projection data of the wide range projection data of parallel beams.

Other embodiments consistent with the present invention will be apparent to those skilled in the art from consideration of the specification and practice of the present invention disclosed herein. It is intended that the specification and examples be considered as exemplary only, with a true scope and spirit of the present invention being indicated by the following claims.

The invention claimed is:

1. An X-ray CT apparatus including an X-ray source for irradiating X-rays onto an object, a multi-slice detector for detecting the irradiated X-rays through an object, a reconstruction unit for reconstructing images based on the projection data collected through the multi-slice detector, and a display unit for displaying reconstructed projection data as a tomography image, the X-ray CT apparatus comprising:
    a first scan unit configured to perform a helical scan over a wide area of a whole diagnosis portion of the object;
    a wide range projection data collecting unit configured to collect projection data of the wide range through the helical scan;
    an ROI designating unit configured to designate a region of interest (ROI) in a reconstructed wide range tomography image displayed on the display;
    a narrow range projection data collecting unit configured to collect narrow range projection data of the ROI through a volume scan by controlling a collimator to provide a single X-ray radiation that covers the designated ROI;
    a wide range projection data generating unit configured to generate regenerated wide range projection data from the reconstructed wide range tomography image; and
    a compounding unit configured to compound the regenerated wide range projection data with the narrow range projection data for display on the display unit.

2. The X-ray CT apparatus according to claim 1, wherein the multi-slice detector includes channel peripheral portions of a first row width along an image slice direction excepting a channel central portion, and channel central portions configured with a second row width along the image slice direction that is wider than the first row width.

3. The X-ray CT apparatus according to claim 1, further comprising:
    a reconstruction process unit configured to perform an image reconstruction process based on the compounded projection data through the compounding unit.

4. The X-ray CT apparatus according to claim 3, wherein the composition unit compounds the narrow range projection data with the regenerated wide range projection data that is regenerated once after reconstructing as an image, based on the volume data stored in the wide range projection data; and
    the reconstruction unit perform the reconstruction process based on the compounded data supplied from the composition unit.

5. The X-ray CT apparatus according to claim 1, wherein the ROI designating unit designates a whole cardiac portion as the region of interest (ROI).

6. The image controlling method for an X-ray CT apparatus according to claim 5, wherein the second multi-slice detector has a plurality of detector elements of more than 200 rows in order to obtain a higher time resolution for the cardiac portion by the volume scan.

7. The X-ray CT apparatus according to claim 1, wherein the multi-slice detector has a plurality of detector elements of more than 200 rows in order to obtain a higher time resolution for the cardiac portion by the volume scan.

8. The X-ray CT apparatus of claim 1, further comprising:
    a control unit configured to cause a second scan unit to perform the volume scan by controlling the collimator to cover the ROI, without moving the object along a body axis of the object.

9. An image controlling method for an X-ray CT apparatus including an X-ray source for irradiating X-rays onto an object, a multi-slice detector for detecting the irradiated X-rays through an object, and a reconstruction unit for reconstructing images based on the projection data collected through the multi-slice detector, the image controlling method comprising:
    executing a helical scan over a whole diagnosis portion of an object;
    collecting projection data of a wide range though the helical scan;
    displaying a wide range tomography image by performing a reconstruction process based on the wide range projection data;
    designating a region of interest (ROI) in the displayed wide range tomography image;
    executing a volume scan on the designated ROI for acquiring narrow range projection data of the ROI by controlling a collimator to provide a single X-ray radiation that covers the designated ROI;
    collecting narrow range projection data of the volume scan on the designated ROI through the multi-slice detector;
    generating regenerated wide range projection data from the reconstructed wide range tomography image;
    compounding the regenerated wide range projection data with the narrow range projection data; and
    displaying an image by performing a reconstruction process on the compounded data.

10. The image controlling method for an X-ray CT apparatus according to claim 9, wherein the wide range projection data is acquired though the multi-slice detector that includes channel peripheral portions of a first row width along an image slice direction excepting a channel central portion, and the narrow range projection data is acquired through the multi-slice detector, which includes the channel central portion configured with a second row width along the image slice direction that is wider than the first row width.

11. The image controlling method for an X-ray CT apparatus according to claim 9, wherein the ROI designating unit designates a whole cardiac portion as the region of interest (ROI).

* * * * *